United States Patent [19]

Dumíc et al.

[11] Patent Number: 5,286,744

[45] Date of Patent: Feb. 15, 1994

[54] N-SULFONYL-TETRAHYDRO-[1,3]-DIOX-EPINO[5,6-B]AZIRINES, INTERMEDIATES FOR THEIR PREPARATION AND THEIR USE

[75] Inventors: Miljenko Dumíc; Darko Filíc, both of Zagreb; Vinkovíc, Cakovec; Blanka Jamnicky, Zagreb, all of Yugoslavia

[73] Assignees: Pliva Handels GmbH, Fed. Rep. of Germany; Pliva, Croatia, Yugoslavia

[21] Appl. No.: 932,482

[22] Filed: Aug. 20, 1992

[30] Foreign Application Priority Data

Aug. 22, 1991 [YU] Yugoslavia ............................ 1433/91

[51] Int. Cl.$^5$ .................... A61K 31/395; C07D 491/02
[52] U.S. Cl. ...................................... 514/450; 548/958; 548/961
[58] Field of Search ................. 548/958, 961; 514/450

[56] References Cited

U.S. PATENT DOCUMENTS 4,389,526  6/1983  Sovak et al. ...................... 549/347
5,142,054  8/1992  Schaffner et al. ...................... 546/15

OTHER PUBLICATIONS

Dumic, et al., A Convenient Method for the Preparation of cis-3,4,8,8a-Tetrahydro-6H[1,3]-Dioxepino[5,6-d]Oxazoles, OPPI Briefs, vol. 24, No. 5 (1992) pp. 536-539.
Dumic, et al., Chemistry of 1,3-Dioxepins. Chemical Abstract, vol. 117 (1992) p. 87.

*Primary Examiner*—Robert W. Ramsuer
*Assistant Examiner*—Jacqueline Haley
*Attorney, Agent, or Firm*—Pollock, Vande Sande & Priddy

[57] ABSTRACT

Starting from cis-2-butene-1,4-diol, via the 4,7-dihydro-1,3-dioxepin and trans-6-acylamino-5-chloro-1,3-dioxepans the novel tetrahydro-[1,3]-dioxepino[5,6-b]-azirines were synthesized, and therefrom the novel hypoglycaemically active N-sulfonyl-tetrahydro-[1,3]-dioxepino[5,6-b]azirines. The inventive compounds are valuable intermediates in the synthesis of other, biologically active substances.

35 Claims, No Drawings

N-SULFONYL-TETRAHYDRO-[1,3]-DIOXEPINO[5,6-B]AZIRINES, INTERMEDIATES FOR THEIR PREPARATION AND THEIR USE

The present invention relates to new N-sulfonyl-tetrahydro-[1,3]-dioxepino[5,6-b]-azirines, to methods and intermediates for their preparation, and to their hypoglycaemic use.

It has been known, that the clinical therapy of noninsulin-dependent diabetes Type II (noninsulin-dependent diabetes mellitus, NIDDM), relies nowadays on only two classes of hypoglycaemic compounds: sulfonylureas and biguanides. [R. SARGES, Progr. Med. Chem. 18, 191 (1981); A. C. ASMAL and A. MARBLE, Drugs, 28, 62 (1984); L. P. KRALL in: Joslin's Diabetes Mellitus, 12th Ed., Lea & Febiger, Philadelphia, 1985, p. 412].

It has been known as well, that representatives of numerous compound classes, such as e.g. thiazolinedione (ciglitzone, pioglitazone; CP-72467), sulfonylimidazoline (CGP 11112), carboxamidine (linoglride); oxiranecarboxylic acids (etomoxir), piridyl ethyl imidazoline (DG 5128), polysaccharides (acarbose), and several others, were introduced into clinical testings of hypoglycaemic activity, yet none came on the market, owing to the insufficient efficacy or other reasons [R. J. MOHRBACHER et al, Ann. Rep. Med. Chem. 22, 213 (1987); E. R. LARSON et al, Ann. Rep. Med. Chem. 25, 205 (1989); K. E. STEINER and E. L. LIEN, Prog. Med. Chem. 24, 209 (1987); S. C. STINSON, Chem. Eng. News, Sep. 30, 1991].

According to the Applicant's own searches on Prior Art the N-sulfonyltetrahydro-[1,3]-dioxepino[5,6-b]azirines of the following formula I represent a novel class of heterocyclic compounds and a new class of potent hypoglycaemics.

The first object of the present invention are new N-sulfonyl-tetrahydro-[1,3]-dioxepino[5,6-b]azirines of the general formula I

I wherein $R^1$ and $R^2$ may stand for a hydrogen atom, a straight or a branched $C_{1-4}$ alkyl, or a phenyl, and $R^1+R^2$ may stand for an alkylidene group, such as e.g. a tetramethylene, a pentamethylene or a hexamethylene group, and $R^3$ may stand for an alkyl group, such as e.g. a methyl or a trifluoromethyl group, or a p-substituted phenyl group

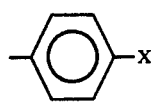

wherein X may stand for a hydrogen atom, a straight or a branched $C_{1-4}$ alkyl, or a halogen atom, such as e.g. fluorine, chlorine, bromine, or iodine, or a nitro, an amino, or an acylamino group, such as e.g. acetylamino, or an alkoxy group, such as e.g. a methoxy group, according to one of the following reactions (Schemes 1–4)

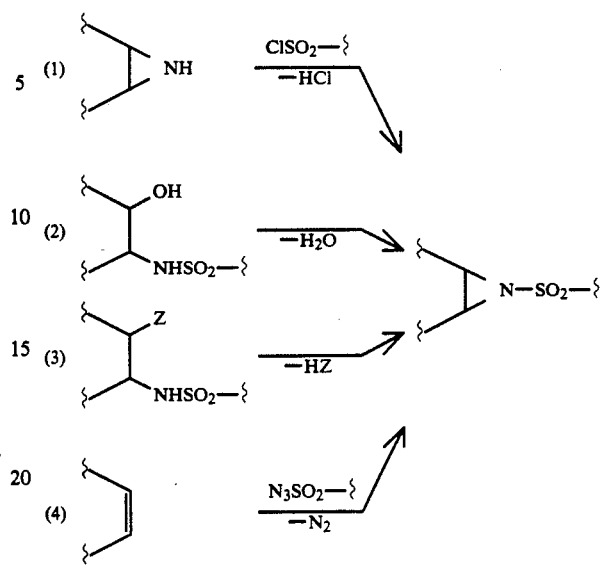

generally known for the N-sulfonyl-azirine synthesis [O. C. Dermer, G. E. Ham, Ethyleneimine and Other Aziridines, Chemistry and Applications, Academic Press, New York, London, 1969; P. E. Fanta, in: A. Weissberger (Ed.), The Chemistry of Heterocyclic Compounds, Vol. 19, Part 1, Interscience Publishers, New York, London, Sydney, 1964., p. 524], especially according to the above process (1) starting from the one the market easily available cis-2-butene-1,4-diol yielding with aldehydes or ketones of the general formula II

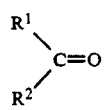

II wherein $R^1$ and $R^2$ have the afore-said meanings, 4,7-dihydro-1,3-dioxepins of the formula III

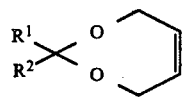

III wherein $R^1$ and $R^2$ have the afore-said meanings, which are subjected to reaction with nitrile chloride in organic nitriles of the formula IV

    IV wherein $R^4$ represents a straight or a branched $C_{1-4}$ alkyl, or a benzyl group, and subjecting the obtained trans-acylamino-chloro-dioxepans of the formula V

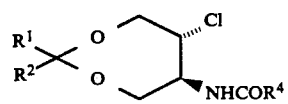

V wherein $R^1$, $R^2$, and $R^4$ have the afore-said meanings, to dehydrohalogenation cyclisation yielding tetrahydro-[1,3]-dioxepino[5,6-b]-azirines of the general formula VI

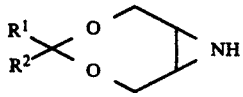

wherein $R^1$ and $R^2$ have the afore-said meanings, which upon the action of sulfochloride of the formula VII

wherein $R^3$ has the afore-said meaning, yield the new N-sulfonyl-tetrahydro-[1,3]-dioxepino[5,6-b]azirines of the formula I, wherein $R^1$ and $R^2$ have the afore-said meanings, and $R^3$ represents a 4-acylaminophenyl group, such as e.g. a 4-acetylaminophenyl group, which are finally subjected to base-catalyzed hydrolysis under the formation of new compounds of the formula I, wherein $R^1$ and $R^2$ have the afore-said meanings, and $R^3$ represents a 4-aminophenyl group (Scheme 5).

epanols [M. SOVAK, R. RANGANATHAN, U.S. Pat. No. 4,389,526 (Jun. 21, 1983), or dioxepino-oxazolines (M. DUMIC et al, Org. Prep. Proc. Int. 24, 545 (1992).]

It has been now surprisingly found, that the new dioxepino-aziridines of the formula VI may be prepared by the transformation of the compounds of the formula V in an aqueous solution of an alkali hydroxide, such as e.g. sodium or potassium hydroxides, at an equimolar ratio of the reactants, up to a 5 fold molar, preferably 1.5-2.5 molar excess of the alkali hydroxide at a temperature within the range 20° C.-150° C., preferably 50°-100° C.

The reaction of the compounds of the formula VI and the sulfochlorides of the formula VII is performed at conditions known per se in the literature, e.g. at stoichometric molar ratios, or at a 1.1-2.0, preferably at a 1.1-1.3 molar excess of the sulfochloride V, with or without an inert organic solvent, such as e.g. aromatic solvents, chosen from toluene or xylene, or chlorinated solvents, chosen from methylenechloride, chloroform

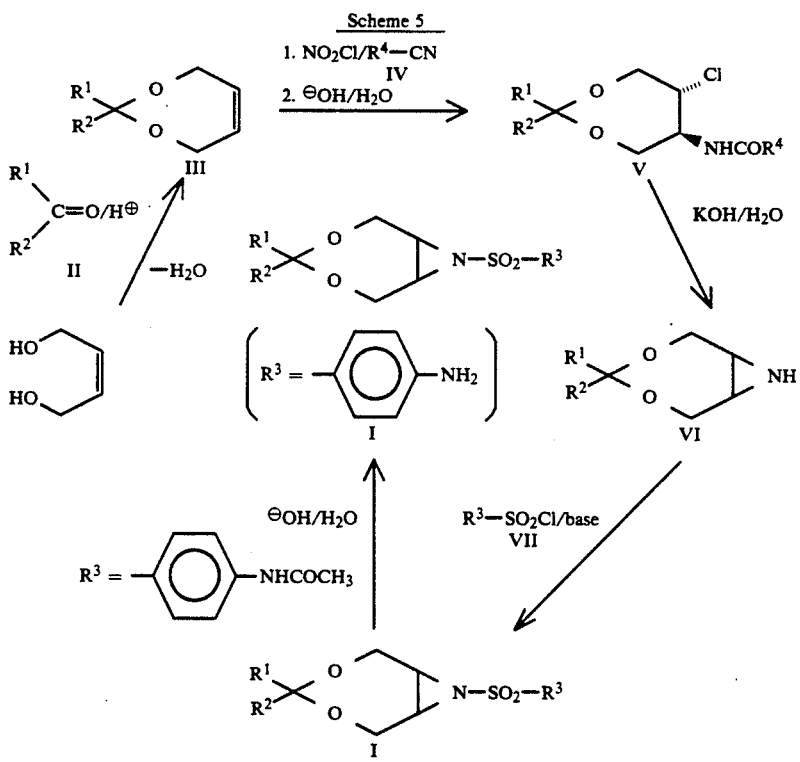

Dioxepins of the formula III are easily available according to the above Scheme 5 by processes known in the literature [C. E.: Pawlosky, Dioxepins and Trioxepins, in: A. Weissberger, E. C. Taylor (Eds.), The Chemistry of Heterocyclic Compounds, Vol. 26, Wiley Interscience, New York, 1972., p. 319].

Trans-acylamino-chlorodioxepans of the formula V are easily available according to the literature data [M. Dumic, M. V. Prostenik, I. Butula, Croat. Chem. Acta. 51, 259, (1978); M. Dumic, Master Thesis, Faculty of Technology, Zagreb University, 1977].

According to the Applicant's investigations the dioxepinoazirines of the formula VI are not known, whereas, their potential precursors of the formula V in the reaction conditions of azirines formation (aqueous soda solution at 100° C., or hot ethanol solution of potassium hydroxide), form vicinal acylamino-dioxor 1,2-dichloroethane, furtheron in ethyl acetate, dioxan, dimethylformamide or dimethylsulfoxide, in the presence of an equimolar quantity or a 1.1-2.0, preferably a 1.1-1.3 molar excess of an organic base, such as e.g. pyridine, triethylamine or morpholine, or in the base used as the solvent. This reaction may be performed also in a 2-5, preferably a 2-3 molar excess of azirine of the general formula VI used as the base for the elimination of the hydrogen chloride generated during the reaction.

The deacylation of the compounds of the general formula I, wherein $R^3$ = 4-acylaminophenyl group, such as e.g. a 4-acetylaminophenyl group, into the compounds of the general formula I, wherein $R^3$ = 4-aminophenyl group, is performed in an alkaline medium by conventional hydrolysis.

A further object of the present invention are new tetrahydro-[1,3]-dioxepino[5,6-b]azirines of the general formula VI suitable as intermediates for the synthesis of biologically active substances, especially hypoglycaemics.

A further object of the present invention is the use of the compounds of the general formula I, as intermediates in the synthesis of biologically active substances, especially hypoglycaemics.

A further object of the present invention is the use of the compounds of the general formula I as active components in pharmaceutical preparations of hypoglycaemic activity.

It was surprisingly found that the present, inventive compounds of the formula I demonstrated a significant or even strong hypoglycaemic activity on the Model of alloxan-induced diabetes in mice and rats, irrespective of the route of application, e.g. intravenous, subcutaneous, or oral. For example, four hours after subcutaneous application of Ia in a dose of 10 mg/kg to mice, the blood glucose (sugar) concentration was diminished for 37%, whereas, the glucose level was 63%, in comparison with untreated, diabetic animals. Forty minutes after the intravenous application of Ia in a dose of 20 mg/kg mice the blood glucose attained even 33% of the value found in untreated, diabetic animals. Six hours after the oral application in a dose of 20 mg/kg mice the compound Ia reduced the blood glucose to 60% of the initial concentration. In an analoguous experiment, four hours after the subcutaneous application in diabetic rats, the compound Ia in a dose of 20 mg/kg rat reduced the blood glucose concentration to 67% of the initial value.

The evaluation experiments on hypoglycaemic activity were performed on CBA strain mice weighting 20–25 g, and Fischer strain rats weighting 160–200 g. They were caged with food and water ad libitum on a lighting schedule of 12 h light: 12 h darkness. Hyperglycaemia was induced by a single injection of alloxan tetrahydrate (65 mg/kg; Merck) into the tail vein (C. C. RERUP, Pharmacol. Rev. 22, 485 (1970)). The animals were subjected to testing 48 hours after alloxan injection. The initial sample of blood (0.025 mL) was taken from the tail vein and immediately the test material (compound of formula I dissolved in a minimum volume of DMSO, and diluted by saline—0.9% NaCl) was given by a single subcutaneous or intravenous injection, or by a stomach tube (per os). Additional blood samples were taken at different intervals (1–24 hours) depending on the dose and the route of application. The blood glucose was assayed by enzymatic method (P. TRINDER, Ann. Clin. Biochem. 6, 24 (1969)). In calculating the results, the blood sugar was expressed as mmole/L of whole blood. The initial blood sample was the control value and was expressed as 100%.

The obtained results on mice are shown in Table 1 below:

TABLE 1

| Compound | s.c. Dose mg/kg | N* | Blood sugar; Percent of Initial; Hours | | |
|---|---|---|---|---|---|
| | | | 1 | 4 | 24 |
| Ia | 5 | 5 | 79 | 99 | 101 |
| | 10 | 6 | — | 63 | — |
| | 20 | 13 | 37 | 53 | 93 |
| Ib | 2 | 6 | 94 | 104 | — |
| | 10 | 5 | 53 | 57 | 88 |
| Ic | 10 | 5 | 76 | 80 | 113 |
| Id | 10 | 6 | 77 | 87 | 87 |
| Ie | 20 | 6 | 107 | 100 | — |
| If | 20 | 6 | 94 | 96 | — |
| Ih | 10 | 5 | 78 | 90 | 116 |
| Ii | 2 | 6 | — | 94 | — |
| | 20 | 5 | — | 68 | 70 |
| Im | 10 | 6 | 85 | 93 | 100 |
| Io | 10 | 5 | 78 | 101 | — |

*N = Number of animals used

On the other hand the substances of the general formula I did not reduce the blood glucose concentration in healthy (nondiabetic control) animals. The testing results of Ia on healthy mice and rats are represented in Table 2 below.

TABLE 2

| Compd. | Animals | Dose and Application | N* | Blood sugar (mmole/L whole blood); Hours | | |
|---|---|---|---|---|---|---|
| | | | | 0 | 1 | 2 |
| Ia | mice | 20 mg/kg; i.v. | 12 | 8.83 ± 0.58 | 8.82 ± 0.91 | — |
| | | 20 mg/kg; s.c. | 6 | 12.43 ± 0.69 | 14.41 ± 0.75 | 13.15 ± 0.72 |
| | | 100 mg/kg; s.c. | 6 | 11.72 ± 2.45 | 12.09 ± 1.01 | 13.17 ± 0.70 |
| Ia | rats | 20 mg/kg; s.c. | 7 | 5.52 ± 0.19 | 5.44 ± 0.18 | — |

*N = Number of animals used.

In view of the afore-said, the new N-sulfonyl-tetrahydro-[1,3]-dioxepino[5,6-b]azirines of the general formula I represent effective hypoglycaemic agents, and may be converted by conventional procedures of pharmaceutical technology into suitable pharmaceutical formulations, such as tablets, pills, powders, troches, capsules, granules, solutions, etc., of short or retarded activity for the treatment of diabetes mellitus.

The present invention is illustrated by the following Examples, which are not to be construed as limiting in any way.

EXAMPLE 1

The mixture consisting of 10.0 g chloroamide V ($R^1=R^2=H, R^4=CH_3$), 7.2 g of potassium hydroxide and 150 cm$^3$ of water was left boiling for 90 minutes under a reflux cooler, and upon cooling to room temperature extracted with chloroform. The evaporation of chloroform and the chromatography of the evaporation residue in a Silica gel column, and the elution with a chloroform/methanol mixture (25:1) yielded the dioxepino-azirine VIa ($R^1=R^2=H$) in the form of a yellowish oil. B.p. 90°–93° C./2.1 kPa.

In an analogous manner, the following tetrahydro-[1,3]-dioxepino[5,6-b]azirines VI were obtained from the corresponding chloroamides V:

TABLE 3

| VI | $R^1$ | $R^2$ |
|---|---|---|
| a | H | H |
| b | H | $CH_3$ |
| c | H | $CH_2CH_3$ |
| d | H | $CH(CH_3)_2$ |
| e | H | Phenyl |
| f | $CH_3$ | $CH_3$ |
| g | —$(CH_2)_4$— | |
| h | —$(CH_2)_5$— | |

TABLE 3-continued

| VI | R$^1$ | R$^2$ |
|---|---|---|
| i | | —(CH$_2$)$_6$— |

EXAMPLE 2

The mixture consisting of 0.120 g of dioxepino-azirine VIa (R$^1$=R$^2$=H), 0.260 g of 4-acetylaminobenzene-sulfochloride, 0.17 g of pyridine, and 5.0 cm$^3$ of methylenechloride was stirred at room temperature for 60 minutes. Upon addition of further 20 cm$^3$ of methylenechloride the mixture was worked up with 2×10 cm$^3$ of sodium hydroxide solution (1:1), the organic layer was separated and washed with 10 cm$^3$ of water, neutralized with diluted hydrochloric acid up to pH=6, washed once more with 10 cm$^3$ of water, and dried over anhydrous sodium sulfate. The evaporation of methylenechloride yielded the crude, chromatographically pure (R$_f$=0.57; eluent: ethyl acetate/methanol=20:1; detection: UV 254 nm, Silica gel plate Merck 60 F$_{254}$) sulfonylazirine Ia (R$^1$=R$^2$=H, R$_3$=4-acetylaminophenyl). M.p. 210°-212° C. (ethyl acetate/methanol=1:1).

Starting from the corresponding azirine VI and sulfochloride VII, the following sulfonylazirines I were synthesized:

TABLE 4

| R$^1$ | R$^2$ | R$^3$ | X | Base | Solvent | Formula I | M.p. (°C.) |
|---|---|---|---|---|---|---|---|
| H | H | —⟨O⟩—X | NHCO—CH$_3$ | Pyridine | — | a | 210-212 |
| | | | | Et$_3$N | CHCl$_3$ | | |
| | | | H | Pyridine | CH$_2$Cl$_2$ | b | 124-127 |
| | | | F | Pyridine | CH$_2$Cl$_2$ | c | 147 |
| | | | Cl | Pyridine | CH$_2$Cl$_2$ | d | 144-146 |
| | | | Br | Pyridine | CH$_2$Cl$_2$ | e | 143-145 |
| | | | CH$_3$ | Pyridine | CH$_2$Cl$_2$ | f | 160 |
| | | | NO$_2$ | Pyridine | CH$_2$Cl$_2$ | g | |
| | | | OCH$_3$ | Pyridine | CH$_2$Cl$_2$ | h | 145-147 |
| H | H | CH$_3$ | | Et$_3$N | — | i | 98-100 |
| | | CF$_3$ | | Et$_3$N | — | j | |
| H | CH$_3$ | —⟨O⟩—X | NHCO—CH$_3$ | Pyridine | CH$_2$Cl$_2$ | k | |
| H | CH$_2$CH$_3$ | | | Pyridine | CH$_2$Cl$_2$ | l | |
| H | CH—(CH$_3$)$_2$ | | | Pyridine | CH$_2$Cl$_2$ | m | 144-146 |
| | | | | Pyridine | CH$_2$Cl$_2$ | n | 240-244 |
| | | | NO$_2$ | Pyridine | CH$_2$Cl$_2$ | o | 143-145 |
| H | Phenyl | | NHCO—CH$_3$ | Pyridine | CH$_2$Cl$_2$ | p | |
| CH$_3$ | CH$_3$ | | | Morpholine | CH$_2$Cl$_2$ | r | 215-217 |
| —(CH$_2$)$_4$— | | | | Pyridine | CH$_2$Cl$_2$ | s | |
| —(CH$_2$)$_5$— | | | | Pyridine | CH$_2$Cl$_2$ | t | |
| —(CH$_2$)$_6$— | | | | Pyridine | CH$_2$Cl$_2$ | u | |

EXAMPLE 3

The mixture consisting of 0.313 g of sulfonylazirine Ia (R$^1$=R$^2$=H, R$^3$=4-acetyl-aminophenyl), 0.140 g of potassium hydroxide, and 3 cm$^3$ of water was kept boiling under reflux for 30 minutes, concentrated into a thick slurry, and extracted with chloroform. The chloroform was evaporated. The chromatography of the evaporation residue in a Silica gel column, and the elution with an ethyl acetate/methanol=20:1 mixture yielded the chromatographically pure (Silica gel Merck 60 F$_{254}$; eluent: ethyl acetate/methanol=20:1; detection: UV 254 nm; iodine vapours: brown colour; Ninhydrin solution: cyclamen-red colour; R$_f$=0.65) sulfonylazirine Iv (R$^1$=R$^2$=H, R$^3$=4-aminophenyl) as a yellowish-reddish oil.

The analogous hydrolysis of the corresponding N-(4-acetylamino-benzenesulfonyl)-azirines of the formula I yielded the following N-(4-amino-benzenesulfonyl)-azirines I:

TABLE 5

| R$^1$ | R$^2$ | R$^3$ | Base | I |
|---|---|---|---|---|
| H | H |  | NaOH | v |
| H | CH(CH$_3$)$_2$ | | NaOH | w |
| CH$_3$ | CH$_3$ | | KOH | z |

We claim:
1. N-sulfonyl-tetrahydro-[1,3]-dioxepino[5,6-b]azirine of the formula I,

$$\underset{R^2}{\overset{R^1}{\diagdown}}\!\!\!\!\times\!\!\!\!\underset{O}{\overset{O\frown}{\diagup}}\underset{\smile}{\phantom{x}}N\text{—SO}_2\text{—R}^3$$

wherein R$^1$ and R$^2$ stand for a hydrogen atom, a straight or a branched C$_{1-4}$ alkyl or a phenyl, or R$^1$ and R$^2$ together form an alkylidene group of 4–6 carbon atoms, R$^3$ stands for a straight or a branched C$_{1-4}$ alkyl, trifluoromethyl group or a p-substituted phenyl group,

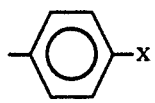

wherein X stands for a hydrogen atom, a straight or a branched C$_{1-4}$ alkyl, fluorine, chlorine, bromine, iodine, nitro, amino, acetylamino or alkoxy group.

2. The compound as claimed in claim 1, wherein R$^1$=R$^2$=H, R$^3$=4-acetylaminophenyl.

3. The compound as claimed in claim 1, wherein R$^1$=R$^2$=H, R$^3$=phenyl.

4. The compound as claimed in claim 1, wherein R$^1$=R$^2$=H, R$^3$=4-fluorophenyl.

5. The compound as claimed in claim 1, wherein $R^1=R^2=H$, $R^3=$4-chlorophenyl.

6. The compound as claimed in claim 1, wherein $R^1=R^2=H$, $R^3=$4-bromophenyl.

7. The compound as claimed in claim 1, wherein $R^1=R^2=H$, $R^3=$4-methylphenyl.

8. The compound as claimed in claim 1, wherein $R^1=R^2=H$, $R^3=$4-nitrophenyl.

9. The compound as claimed in claim 1, wherein $R^1=R^2=H$, $R^3=$4-methoxyphenyl.

10. The compound as claimed in claim 1, wherein $R^1=R^2=H$, $R^3=CH_3$.

11. The compound as claimed in claim 1, wherein $R^1=R^2=H$, $R^3=CF_3$.

12. The compound as claimed in claim 1, wherein $R^1=R^2=H$, $R^3=$4-aminophenyl.

13. The compound as claimed in claim 1, wherein $R^1=H$, $R^2=CH_3$, $R^3=$4-acetylaminophenyl.

14. The compound as claimed in claim 1, wherein $R^1=H$, $R^2=CH_2CH_3$, $R^3=$4-acetylaminophenyl.

15. The compound as claimed in claim 1, wherein $R^1=H$, $R^2=CH(CH_3)_2$, $R^3=$4-acetylaminophenyl.

16. The compound as claimed in claim 1, $R^1=H$, $R^2=CH(CH_3)_2$, $R^3=$4-nitrophenyl.

17. The compound as claimed in claim 1, wherein $R^1=H$, $R^2=CH(CH_3)_2$, $R^3=$4-aminophenyl.

18. The compound as claimed in claim 1, wherein $R^1=H$, $R^2=$phenyl, $R^3=$4-acetylaminophenyl.

19. The compound as claimed in claim 1, wherein $R^1=R^2=CH_3$, $R^3=$4-acetylaminophenyl.

20. The compound as claimed in claim 1, wherein $R^1=R^2=CH_3$, $R^3=$4-aminophenyl.

21. The compound as claimed in claim 1, wherein $R^1$, $R^2=-(CH_2)_4-$, $R^3=$4-acetylaminophenyl.

22. The compound as claimed in claim 1, wherein $R^1$, $R^2=-(CH_2)_6-$, $R^3=$4-acetylaminophenyl.

23. Tetrahydro-[1,3]-dioxepino[5,6-b]azirine of the formula VI

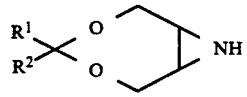

VI wherein $R^1$ and $R^2$ have the meanings, as stated in claim 1.

24. The compound as claimed in claim 23, wherein $R^1=R^2=H$.

25. The compound as claimed in claim 23, wherein $R^1=H$, $R^2=CH_3$.

26. The compound as claimed in claim 23, wherein $R^1=H$, $R^2=CH_2CH_3$.

27. The compound as claimed in claim 23, wherein $R^1=H$, $R^2=CH(CH_3)_2$.

28. The compound as claimed in claim 23, wherein $R^1=H$, $R^2=$phenyl.

29. The compound as claimed in claim 23, wherein $R^1=R^2=CH_3$.

30. The compound as claimed in claim 23, wherein $R^1$, $R^2=-(CH_2)_4$.

31. The compound as claimed in claim 23, wherein $R^1$, $R^2=-(CH_2)_5$.

32. The compound as claimed in claim 23, wherein $R^1$, $R^2=-(CH_2)_6$.

33. The compound as claimed in claim 1, wherein $R^1$, $R^2=-(CH_2)_5-$, $R^3=$4-acetylaminophenyl.

34. The compound of claim 1 wherein said alkylidene group is selected from the group consisting of tetramethylene, pentamethylene and hexamethylene; said alkyl group of $R^3$ is methyl; said alkoxy group is methoxy.

35. Pharmaceutical preparation having hypoglycemia activity which comprises as an active component an effective amount of an azirine as claimed in claim 1 and a pharmaceutically acceptable carrier.

* * * * *